United States Patent [19]
Hoff

[11] Patent Number: 5,470,973
[45] Date of Patent: Nov. 28, 1995

US005470973A

[54] SYNTHESIS OF SULFONAMIDE INTERMEDIATES

[75] Inventor: Roman Hoff, Lausen, Switzerland

[73] Assignee: Alcon Laboratories, Inc., Fort Worth, Tex.

[21] Appl. No.: 317,043

[22] Filed: Oct. 3, 1994

[51] Int. Cl.⁶ .................................................. C07D 513/04
[52] U.S. Cl. ........................................................ 544/48
[58] Field of Search .................................................. 544/48

[56] References Cited

U.S. PATENT DOCUMENTS

| | | | |
|---|---|---|---|
| 5,153,192 | 10/1992 | Dean et al. | 514/226.5 |
| 5,240,923 | 8/1993 | Dean et al. | 514/226.5 |
| 5,344,929 | 9/1994 | Dean et al. | 544/48 |

OTHER PUBLICATIONS

Jones, et al., *J. Org. Chem.* 56, 763–769 (1991).
Corey, *J. Org. Chem.* 53, 2861–2863 (1988).

*Primary Examiner*—John M. Ford
*Attorney, Agent, or Firm*—Sally Yeager

[57] ABSTRACT

Enantioselective syntheses of (S)-6-chloro-3,4-dihydro-2-(3-methoxypropyl)-2H-thieno[3,2-e]-1,2-thiazin-4-ol, 1,1-dioxide and related compounds are described.

3 Claims, No Drawings

SYNTHESIS OF SULFONAMIDE INTERMEDIATES

This invention is directed to the enantioselective synthesis of (S)-3,4-dihydro-2-(3-methoxypropyl)-2H-thieno[3,2-e]-1,2-thiazin-4-ol 1, 1-dioxide and related compounds.

BACKGROUND OF THE INVENTION

The chiral(S)-tetrahydro-1-methyl-3,3-diphenyl-1H,3H-pyrrolo-[1,2-c]1,3,2-oxazaborole (oxazaborole$_1$) catalyzed borane reduction and reduction using (+) or (−) B-chlorodiisopinocampheylborane are two of the most effective methods for the enantioselective reduction of ketones to alcohols. With both methods the degree of enantiomeric purity obtained is dependent on the structure of the ketone.

The enantiomerically pure alcohol 1 is an important intermediate for the synthesis of (R)-4-(ethylamino)-3,4-dihydro-2-(3-methoxypropyl)-2H-thieno[3,2-e]-1,2-thiazin-6-sulfonamide 1, 1-dioxide and related compounds, which are useful in the treatment of ocular hypertension and glaucoma as disclosed in U.S. Pat. Nos. 5,240,923 and 5,153,192.

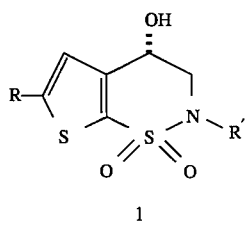

1 wherein:

R is H or Cl; and

R' is $C_{1-6}$ alkyl, $CH_2(CH_2)_nOR''$, wherein R'' is $CH_3$ or $(CH_2)_nCH_3$ and n is 1–4, $CH_2(CH_2)_nX$, wherein X is Br, Cl, or I, and n is 1–4, or $(CH_2)_nAr$, wherein Ar is unsubstituted phenyl, 3-methoxyphenyl, or 4-methoxyphenyl and n is 1 or 2.

Synthesis of 1 can be accomplished via an enantioselective reduction of 3-(bromoacetyl)-2-thiophenesulfonamide 2 with (+)-B-chlorodiisopinocampheylborane [(+)-DIP-Chloride™], followed by cyclization and N-alkylation with 3-bromo-1-methoxypropane. (See commonly assigned U.S. Pat. Nos. 5,240,923 and 5,153,192.) The method of the present invention has advantages over these procedures in that it is a catalytic reaction versus a reaction requiring a stoichiometric or excess amount of the reducing agent.

Commonly assigned U.S. Pat. No. 5,344,929 discloses the synthesis of 1 via a (+)-DIP-Chloride™ reduction of the bromo ketone 2 followed by cyclization to the cyclic chiral alcohol 8 and alkylation to 1. The method of the present invention (Scheme 1) involves the preparation of a racemic cyclic alcohol 4 followed by N-alkylation, oxidation to ketone 6, and re-reduction with oxazaborole$_1$ reagent to give 1. The present process avoids the use of (+)-DIP-Chloride™.

The same sequence of reaction steps using borane tetrahydrofuran and catalytic amounts of oxazaborole$_1$ gives less enantiomerically pure compound 1 even with different amounts of catalyst and at lower reaction temperature.

The present invention involves the synthesis of 1 with high enantioselectivity at about 30° C. within a shortened reaction time and at a lower cost than prior methods. In addition, the precursor of the catalyst can be recovered by known procedures, see Jones, et al., *J. Org. Chem.* 56, 763–769 (1991) and Corey, *J. Org. Chem.* 53, 2861–2863 (1988).

SUMMARY OF THE INVENTION

This invention is concerned with a novel process for preparing 1 at a relatively low cost and with high enantiomeric purity. The process starts with ketone 2, which is converted to racemic 3-(2-bromo-1-hydroxyethyl)-2-thiophenesulfonamide 3. Cyclization to racemic-3,4-dihydro-2H-thieno[3,2-e]-1,2-thiazin-4-ol 1, 1-dioxide 4 and N-alkylation with 3-bromo-1-methoxypropane leads to 5. 5 is then oxidized with chromic acid to achieve ketone 6. 6 is then treated with boran-tetrahydrofuran and catalytic amounts of either oxazaborole$_1$, or (S)-tetrahydro-1,3,3-triphenyl-1H,3H-pyrrolo [1,2-c]1,3,2 oxazaborole (oxazaborole$_2$) to provide 1.

A second method (Scheme 2) starts with ketone 2, which is reduced with borane-tetrahydrofuran and oxazaborole$_1$, to give enantiomeric enriched 9, which was not isolated, and cyclized with aqueous sodium hydroxide to give enantiomeric enriched 8, which is then N-alkylated with 3-bromo-1-methoxypropane to give 1.

A third method (Scheme 3) starts directly with oxidation of 4 to produce 7, which is reduced with oxazaborole$_1$ catalyst to give 8, which is alkylated to give 1.

DETAILED DESCRIPTION OF THE INVENTION

The preferred method of the present invention is described by Scheme 1.

Scheme 1:

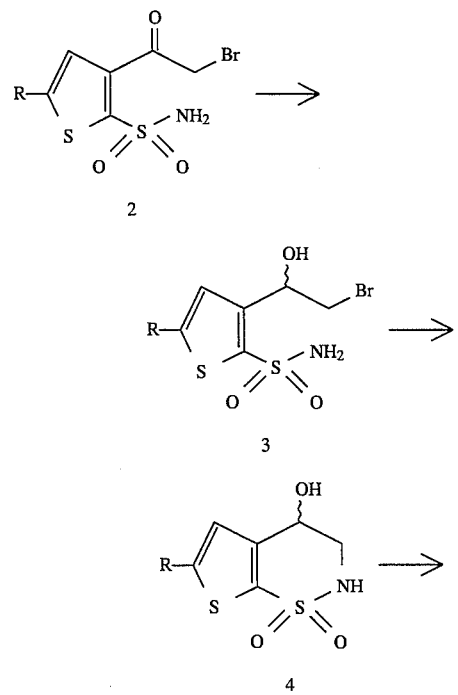

3

-continued

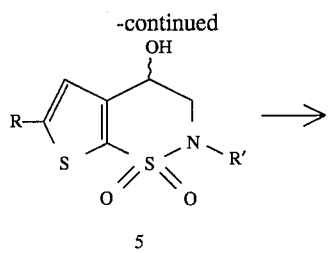
5

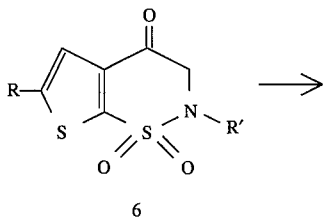
6

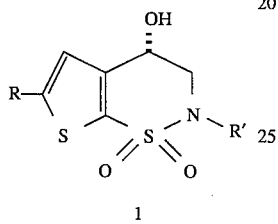
1 wherein:

R is H or Cl; and

R' is $C_{1-6}$ alkyl, $CH_2(CH_2)_nOR''$, wherein R'' is $CH_3$ or $(CH_2)_nCH_a$ and n is 1–4, $CH_2(CH_2)_nX$, wherein X is Br, Cl, or I, and n is 1–4, or $(CH_2)_nAr$, wherein Ar is unsubstituted phenyl, 3-methoxyphenyl, or 4-methoxyphenyl and n is 1 or 2.

Compound 1 can also be prepared according to the following two procedures set forth in Schemes 2 and 3 with R, R', and R'' as defined above.

Scheme 2:

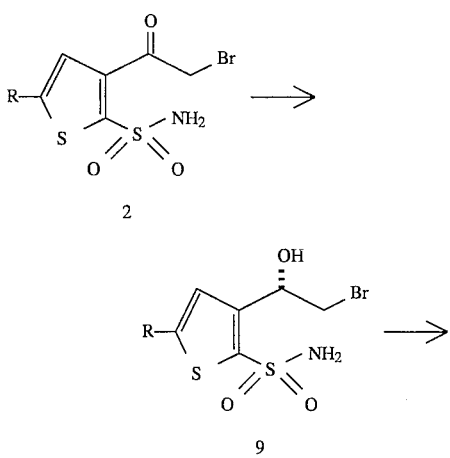

4

-continued

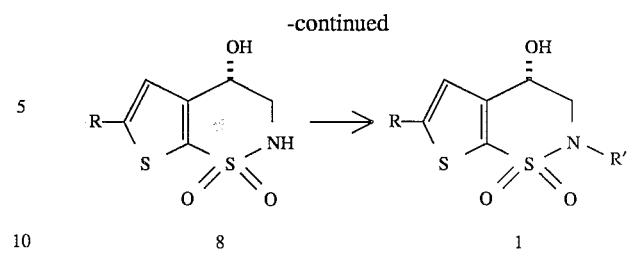
8   1

Scheme 3:

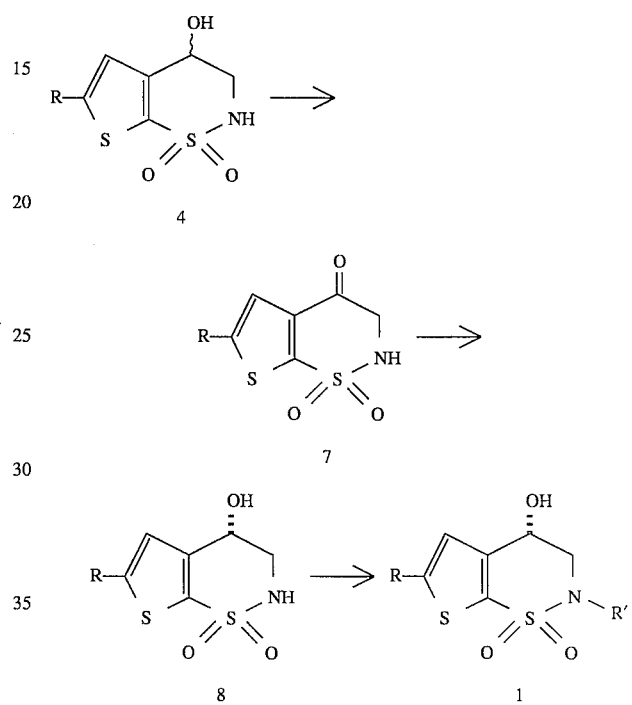

In the following examples, melting points were determined on a Gallenkamp melting point apparatus and are uncorrected. IR spectra were recorded on a Perkin-Elmer-297 infrared spectrometer. NMR-Spectra were recorded in $CDCl_3$ and $D_6$-acetone ($^{13}C$, $^1H$) on a Bruker ARX 400 spectrometer. $^1H$ chemical shifts are reported in ppm from internal standard of residual chloroform (7.27 ppm) and acetone (2.01 ppm). $^{13}C$ chemical shifts are reported in ppm from the central peak of deuterochloroform (77.0 ppm) or deuteroacetone (29.8 ppm). Tris-[3-(trifluormethylhydroxymethylene)-d-camphorato]-europium-(III) was used as chemical shift reagent and purchased from Fluka. Specific rotations were determined on a Schmidt & Haensch polarimeter from the pure liquids. Analytical gas chromatography (GC) was carried out on a Perkin-Elmer 8700 gas chromatograph equipped with a split mode injector for capillary columns, an on-column injector for packed columns, and a flame-ionization detector, with helium as carrier gas. The following columns were used: 25 m×0.32 mm FS-OV-1-0.25 (Macherey & Nagel) and 5'⅛'2 mm GE SE-52 (Macherey & Nagel). Analytical high-performance liquid chromatography (HPLC) was carried out on a Merck Hitachi model D 6000 with a D 6000 Interface using the following columns: 4×125 mm LiChroCart 250-4(Merck) Spherisorb ODS-2 (5 mm) and 4×250 mm LiChroCart 250-4

(Merck) ChiraDex (5 mm). Analytical thin layer chromatography (TLC) was carried out with TLC-aluminum sheets silica 60 $F_{254}$ using the following solvent system: n-hexane/ethyl acetate 1:1 or n-hexane/acetone 1:1. Visualization was accomplished with UV-light. (S)-Tetrahydro-1-methyl-3,3-diphenyl- 1H,3H-pyrrolo[1,2-c][1,3,2]oxazaborole was obtained from Callery Chemical Company U.S.A. or prepared according to the literature. 3-Bromoacetyl-5-chloro-2-thiophensulfonamide 2 (R=Cl) was obtained from Amcis AG, Switzerland.

In the following examples R is Cl and R' is $CH_2(CH_2)_2OCH_3$.

EXAMPLE 1

6-chloro-3,4-dihydro-2H-thien[3,2-e]-1,2-thiazin-4-ol 1, 1-dioxide 4

In a 4.5 L three necked flask fitted with a reflux condenser, thermometer and dropping funnel 159 g ketone 2 were dissolved in 1.5 L ethanol. To the stirred solution, which retains some undissolved ketone 2, were added in small portions 10.7 g sodium borohydride. During this time the reaction mixture first became red-brown and then a clear yellow solution. At the same time $H_2$ evolved and the temperature rose to 40° C. Stirring was continued for 1 h during which the temperature dropped to 28° C. Then 1.5 L of 1N aqueous sodium hydroxide solution were added within 15 min. During this time the temperature rose again to 35° C. and a small amount of sodium hydroxide separated at the bottom of the flask (saturation). After a further 5 min. the ethanol was evaporated under vacuum and the residual aqueous solution was acidified with about 1.1 L of 1N hydrochloric acid to pill. The separating brown oil was 1× extracted with 600 mL ethyl acetate and 1× with 300 mL. The clear aqueous solution was discarded and the extracts dried over sodium sulfate. After filtration the solvent was evaporated and crystallization induced by dissolving and stirring in 250 mL of dichloromethane. The solid was separated by filtration and washed with dichloromethane. After drying the residue weighed 94 g (88%). This raw material was used without further purification. The identity of this racemic 4 was elucidated by comparison with IR-spectra and TLC of enantiomerically pure 8.

EXAMPLE 2

6-chloro-3,4-dihydro-2-(3-methoxypropyl)-2H-thieno-[3,2-e]-1,2-thiazin-4-ol 1, 1-dioxide 5

Into a 250 mL three necked flask fitted with thermometer and reflux condenser 19.6 g of alcohol 4 were dissolved in 100 mL dimethylsulfoxide, then 33.9 g potassium carbonate and 15.3 g of 1-bromo-3-methoxypropane were added. During this period the temperature rose to about 30° C. and stirring was continued through the night. After 22 h the mixture was poured into 960 mL of saturated sodium chloride solution and then twice extracted with 220 mL of t-butyl methyl ether. The combined extracts were then washed with 100 mL of 10% aqueous sodium hydroxide solution, 80 mL of 2.5% sodium hypochlorite solution and then with 60 mL of saturated sodium chloride solution. After drying with sodium sulfate and filtration the solvent was evaporated in vacuum. The residue was used without further purification; yield 23.5 g (92%). Identification was made by comparison between the IR-spectra of compounds 5 and 1.

EXAMPLE 3

6-chloro-2,3-dihydro-2-(3-methoxypropyl)-4H-thieno-[3,2-e]-1,2-thiazin-4-one 1, 1-dioxide 6

243 g of alcohol 5 were dissolved in 1.56 L t-butyl methyl ether and charged into a 4-L three necked flask fitted with a reflux condenser and a thermometer. With stirring and cooling with an ice bath a mixture consisting of 155 g of sodium dichromate and 206 g sulfuric acid dissolved in 546 mL of water was added. The temperature was maintained below 20° C. during the addition. After the addition of chromic acid, the biphasic mixture was stirred for further 90 min at 25° C. until the TLC indicated complete consumption of the racemic alcohol 5. Then the aqueous layer was separated and 4× extracted with 390 mL of t-butyl methyl ether. The combined ethereal solutions were successively washed with 624 mL of saturated sodium bicarbonate and sodium chloride solution, respectively. After drying with sodium sulfate and filtration the solvent was evaporated. Crystallization of the residual oil was induced by addition of a few crystals of authentic ketone 6 and about 25 mL of diethyl ether. To complete the crystallization 400 mL of n-hexane were added. An analytical sample was recrystallized from diethyl ether, mp: 48°–52° C., yield: 194 g (80%).

EXAMPLE 4

6-Chloro-2,3-dihydro-4H-thieno[3,2-e]-1,2-thiazin-4-one 1, 1-dioxide 7

Ketone 7 was prepared from 4 in the same manner as mentioned for ketone 6, yield 61%.

EXAMPLE 5

(S)-6-Chloro-3,4-dihydro-2-(3-methoxypropyl)-2H-thieno[3,2-e]-1,2-thiazin-4-ol 1, 1-dioxide 1

Into a thoroughly dried four necked flask (750 mL) fitted with two dropping funnels, a reflux condenser, and a thermometer trader an argon atmosphere were placed 2.07 g of oxazaborole$_1$ and 15 mL of tetrahydrofuran. From one of the dropping funnels, which was filled with 250 mL of borane tetrahydrofuran complex solution, 25 mL of this solution were released into the reaction vessel. The second dropping funnel contained 116 g of ketone 6 dissolved in 250 mL of tetrahydrofuran. Simultaneously from both dropping funnels these prepared solutions were then added dropwise to the reaction vessel within ½ h. The temperature of the reaction mixture was held below 33° C. with an ice water bath. The mixture was stirred for another 5 min and then quenched with 55 mL of methanol. Then the solution was washed with sodium chloride, sodium bicarbonate, and then again with sodium chloride (190 mL of saturated solutions, respectively). The ethereal solution was then dried with sodium sulfate, filtered, and the solvent evaporated in vacuum. The residue was purified on a silica (1 kg) column with n-hexane/ethyl acetate 1:1 as eluent; yield: 112 g (90%); $[\alpha]^{22}_D$=+ 20.97° (91.6% ee). The enantiomeric purity determined by HPLC and $^1$H-NMR with chemical shift reagent was greater than 94% ee.

EXAMPLE 6

(S)-6-chloro-3,4-dihydro-2-(3-methoxypropyl)-2H-thieno[3,2-e]-1,2-thiazin-4-ol 1, 1-dioxide 1

Starting with 9.3 g of ketone 6 and following the same procedure as mentioned in Example 5 except using a stock solution of 1M (S)-tetrahydro-1,3,3-triphenyl- 1H,3H-pyrrolo[1,2-c][1,3,2]oxazaborole as catalyst led to 1, 4.9 g (52%) yield, ee=65%.

EXAMPLE 7

(S)-6-Chloro-3,4-dihydro-2H-thieno[3,2-e]-1,2-thiazin-4-ol 1, 1-dioxide 8

Starting with 7.13 g of ketone 7, following the same procedure as mentioned in Example 5, led to 5.84 g (81%) of alcohol 8; ee 71.5% determined by HPLC.

EXAMPLE 8

Starting with ketone 2 and following the same procedure mentioned in Example 5 except that variable amounts of the catalyst (1.0, 2.0, 5.0, and 10.0 mol %) were used at different temperatures, after cyclization according the method using (+)- B-chlorodiisopinocampheylborane, gave ee-values less than 59%.

I claim:

1. A process for making a compound of formula:

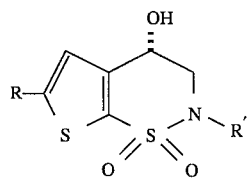

1 wherein:

R is H or Cl; and

R' is $C_{1-6}$ alkyl, $CH_2(CH_2)_nOR''$, wherein R'' is $CH_3$ or $(CH_2)_nCH_3$ and n is 1–4, $CH_2(CH_2)_nX$, wherein X is Br, Cl, or I, and n is 1–4, or $(CH_2)_nAr$, wherein Ar is unsubstituted phenyl, 3-methoxyphenyl, or 4-methoxyphenyl and n is 1 or 2, which comprises:

a. reducing 3-bromoacetyl)-2-thiophenesulfonamide 2 to racemic 3-(2-bromo- 1-hydroxyethyl)-2-thiophenesulfonamide 3 with sodium borohydride;

b. cyclizing 3 to racemic 3,4-dihydro-2H-thieno[3,2-e]-1,2-thiazin-4-ol 1,1 -dioxide 4 with sodium hydroxide;

c. N-alkylating 4 in dimethylsulfoxide in the presence of potassium carbonate to give 3,4-dihydro-2-alkyl-2H-thieno[3,2-e]-1,2-thiazin-4-ol 1,1-dioxide 5;

d. oxidizing 5 to 2,3-dihydro-2-alkyl-4H-thieno[3,2-e]-1,2-thiazin-4-one 1,1-dioxide 6 with sodium dichromate;

treating 6 with boran tetrahydrofuran and a catalytic amount of (S)-tetrahydro-1-methyl-3,3-diphenyl-1H,3H-pyrrolo-[1,2-c]1,3,2 oxazaborole or (S)-tetrahydro-1,3,3-triphenyl-1H,3H-pyrrolol[1,2-c]1,3,2 oxazaborole to provide 1.

2. The process of claim 1 wherein 6 is treated with (S)-tetrahydro-1-methyl-3,3-diphenyl-1H,3H-pyrrolo-[1,2-c]1,3,2 oxazaborole.

3. The process of claim 1 wherein 6 is treated with (S)-tetrahydro-1,3,3-triphenyl- 1H,3H-pyrrolo-[1,2-c]1,3,2 oxazaborole.

* * * * *